United States Patent [19]

Bragg

[11] 4,151,851
[45] May 1, 1979

[54] DENTAL FLOSSING TOOL

[76] Inventor: Kenneth R. Bragg, 635 Pasco De La Playd, Redondo Beach, Calif. 90274

[21] Appl. No.: 674,889

[22] Filed: May 27, 1976

[51] Int. Cl.² .............................................. A61C 15/00
[52] U.S. Cl. ...................................................... 132/91
[58] Field of Search ...................... 132/91, 92, 89, 90, 132/83 R; 206/63.5

[56] References Cited

U.S. PATENT DOCUMENTS

| | | | |
|---|---|---|---|
| 2,467,221 | 4/1949 | Pastl | 132/92 R |
| 3,340,881 | 9/1967 | Cowan | 132/92 R |
| 3,393,687 | 7/1968 | Whitman | 132/91 |
| 3,534,745 | 10/1970 | Waters | 132/92 R |
| 3,746,017 | 7/1973 | Casselman | 132/92 A |
| 3,799,177 | 3/1974 | Bragg | 132/92 R |
| 3,906,963 | 9/1975 | Jenkins | 132/92 R |
| 3,927,687 | 12/1975 | Thierman | 132/92 A |
| 3,939,853 | 2/1976 | Spanondis | 132/91 |

FOREIGN PATENT DOCUMENTS

| | | | |
|---|---|---|---|
| 735125 | 4/1932 | France | 132/91 |
| 1035074 | 4/1953 | France | 132/83 R |

*Primary Examiner*—G.E. McNeill
*Attorney, Agent, or Firm*—John N. Wolfram

[57] ABSTRACT

A dental flossing tool that includes two sticks. A supply of floss stored in a hollow handle on one of the sticks is fed to a place of use between the sticks by the use of two spools, one each rotatably mounted on each stick. One spool withdraws fresh floss from the storage handle and the other collects and stores the used floss. The collecting spool has a cutter mounted thereon and has notches for aligning the floss with the cutter. The sticks have slits for entering the floss into openings that support the floss for use in a person's mouth, and the floss is stored on the tool with substantially no twist in the filaments of the floss strand and is withdrawn in a manner to avoid applying a twist. Portions of the tool may have a distinctive color for identification purposes and also for making the aforesaid notches clearly visible. The hollow handle not being used to store the floss may have a colored card therein to provide an alternative method of identifying one person's tool from that of another. The collecting spool may have a wedging groove therein for gripping the floss or it may have a hinged cap that wedges the floss between the cap and the spool body.

9 Claims, 18 Drawing Figures

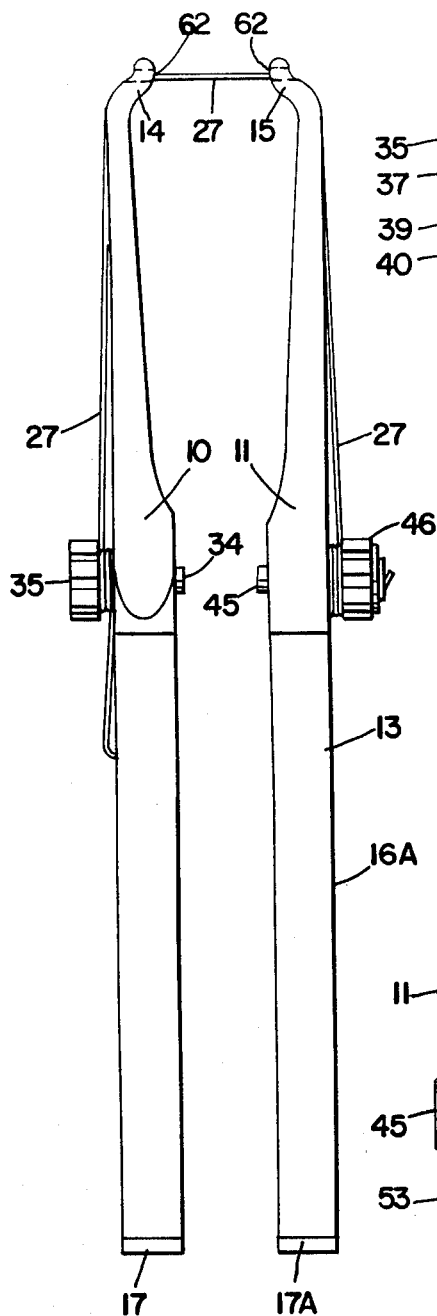
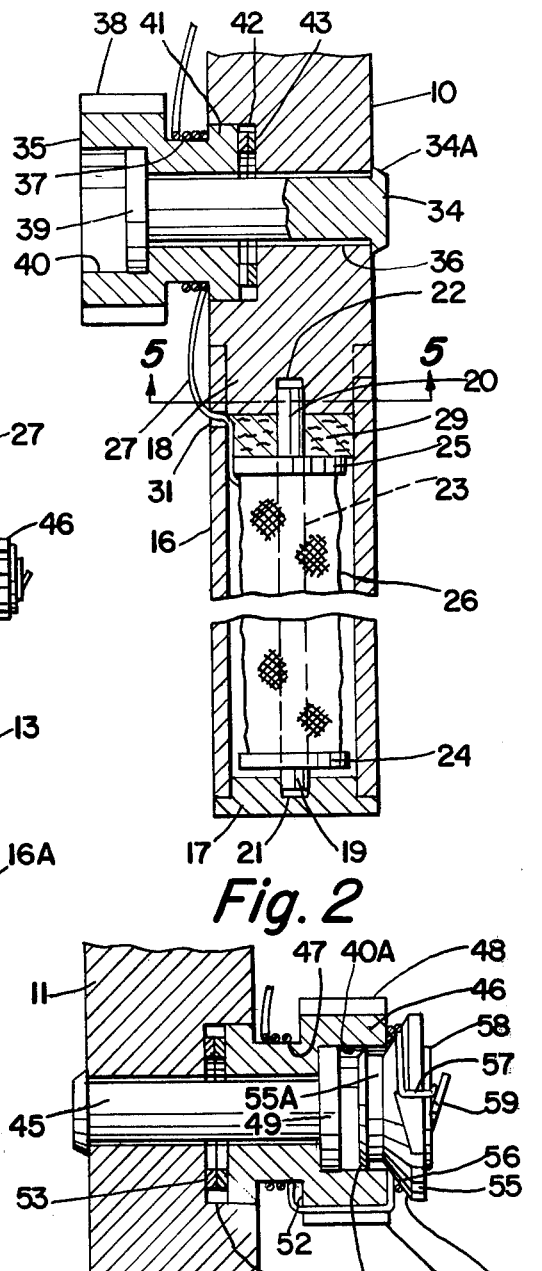
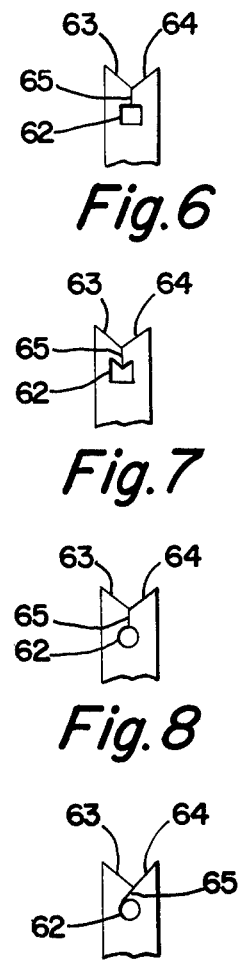
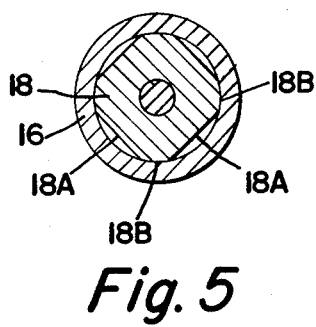
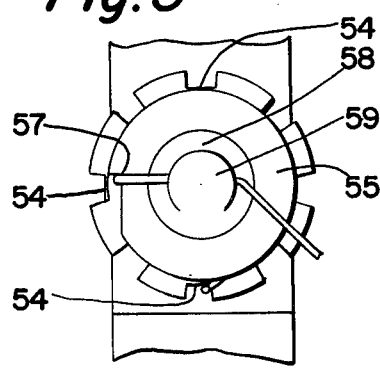

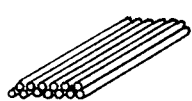
Fig.10
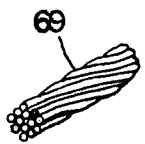
Fig.11
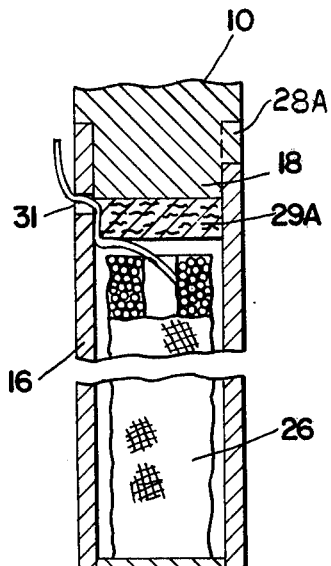
Fig.12
Fig.13
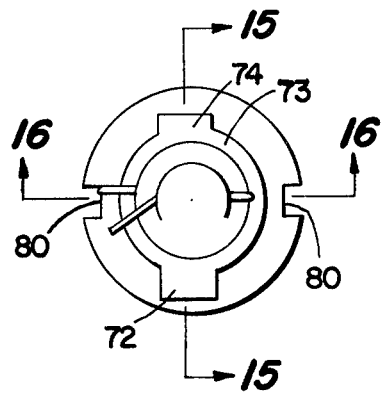
Fig.14
Fig.15
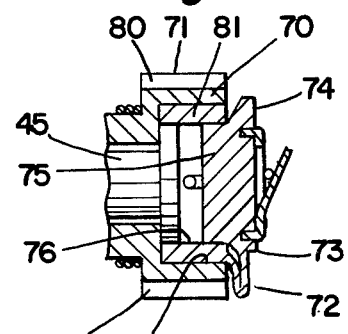
Fig.16
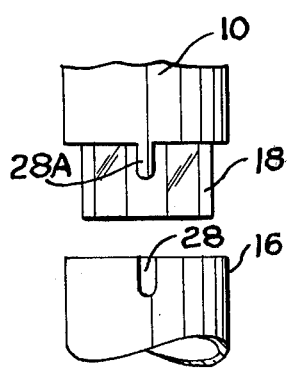
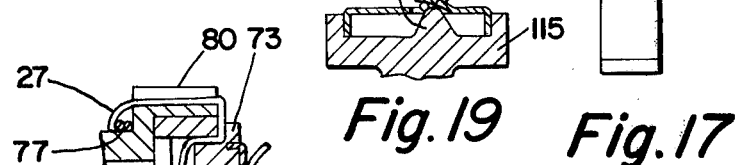
Fig.19   Fig.17
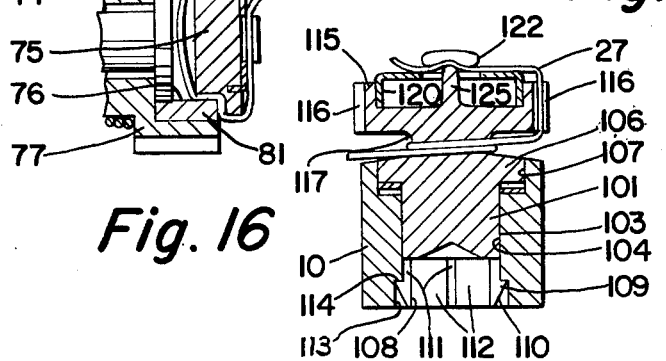
Fig.18

DENTAL FLOSSING TOOL

BACKGROUND OF THE INVENTION

The flossing tools disclosed in my U.S. Pat. No. 3,799,177 employ a body means that includes two sticks that may be either separate or mounted on a common body. Each stick has a finger or tip insertible into a person's mouth. A supply of floss strand is stored within a handle and from which the strand may be fed first to a securing device, then to the tips and finally to another floss securing device. Although such tools conserve floss and are of advantage for manipulating the floss in a person's mouth, the securing devices are not conveniently operable for advancing fresh floss to the place of use at the tips or for changing the length of floss between the tips while the tools are in use, nor is there a convenient provision for collecting and storing used floss. Also, the provision for storing the fresh floss supply does not comtemplate use of floss with filaments parallel to the axis of the floss strand, nor does the floss supporting means on the tips permit ready insertion of the floss into the support means.

SUMMARY OF THE INVENTION

This invention improves the forms of flossing tools disclosed in my U.S. Pat. No. 3,799,177 by providing for storage and withdrawal of floss from a handle on one of the sticks in an untwisted condition, providing a pair of rotatable spools, one for withdrawing fresh floss from the storage handle and the other for collecting used floss, and which spools are readily operable by a person's finger tips for advancing fresh floss to the place of use and for changing the length of floss between the tips while holding the sticks in positions of use. The collecting spool has notches thereon for guiding the floss to a cutter on the spool that is used to cut off excess used floss. The tips of the sticks are slit and specially formed to permit ready insertion of the floss into the floss support means thereon. Caps on the spools and/or handles may be of different colors for identifying one tool from another, or a colored card may be inserted in the one hollow handle for this purpose. The collecting spool may have a wedging groove therein for gripping the floss or it may have a hinged cap that wedges the floss against the spool body. The hollow handle that contains the floss supply is readily mountable and demountable on the respective stick and has a side opening through which the floss strand may be led to the withdrawal spool. This handle also has a notch to receive a lug on the respective stick for aligning the side opening angularly relative to the withdrawal spool. A fibrous pad in the hollow storage handle frictionally engages the floss strand to prevent unwanted withdrawal of floss from the storage handle.

In modified forms of the tool the two sticks may be joined, either integrally or with the one stick pivoted on the other and but one handle provided in either case.

DETAIL DESCRIPTION

FIG. 1 is a side view of the complete tool that comprises two separate sticks.

FIG. 2 is an enlarged cross section of the floss storage means in a handle on one of the sticks and also showing a cross section of the withdrawal spool.

FIG. 3 is an enlarged cross section of one form of the floss collecting spool and FIG. 4 is a plan view thereof.

FIG. 5 is a cross section on line 5—5 of FIG. 2.

FIGS. 6, 7, 8 and 9 show several forms of structures for supporting the floss at the place of use at the upper end of each stick.

FIG. 10 is a perspective view of a floss strand with filaments parallel to its axis and FIG. 11 is a similar view of a floss strand with filaments spiralled about its axis.

FIG. 12 is a cross section view of a modified arrangement for storing floss in the handle of one of the sticks.

FIG. 13 is a fragmentary side view of a stick and storage handle showing a notch and lug for angularly locating the handle relative to the stick.

FIG. 14 is a plan view of an alternate form of the collecting spool and FIGS. 15 and 16 are cross section views respectively along lines 15—15 and 16—16 of FIG. 14.

FIG. 17 shows a modified form of the tool.

FIG. 18 is a cross section view of a further modified form of the collecting spool and FIG. 19 is a fragmentary section view on the lines 19—19 of FIG. 18.

The form of the tool illustrated in FIG. 1 has a body means that comprises two separate sticks 10 and 11, each stick respectively including a detachable handle 12, 13 at its lower end and a respective tip 14, 15 at its upper end. Handle 12 comprises a tube 16 closed at its lower end by a cap 17 press fitted into the tube. Tube 16 has an open upper end in which a plug portion 18 of stick 10 is press fitted so as to be detachable. As shown in FIG. 5, plug portion 18 is preferably formed with four flats 18A and with rounded portions 18B therebetween that have a tighter press fit with the inside wall of tube 16 than would be practical if plug portion 18 is cylindrical. Tube 16, which is made of clear vinyl plastic, may yield to assume an out of round condition at its upper end to accommodate the tight contact at portions 18B with less tension stresses in the tube than if plug 18 were cylindrical.

Handle 13 comprises a tube 16A identical to tube 16 of handle 12 and attached to stick 11 in the same manner that tube 16 is attached to stick 10. It may contain an extra spool of floss for later transfer to tube 16 or it may contain a card of given color or with marking to identify the tool with respect to a particular individual.

Rotatably mounted in tube 16 with spindle portions 19, 20 journalled in recesses 21, 22 in cap 17 and plug 18 is a spool 23 having flanges 24, 25 for retaining a supply of floss 26 wound onto the spool to form a coil. A circular pad 29 of fibrous material is supported on spindle 20 and snugly engages tube 16.

Pad 29 frictionally engages floss strand 27 leading from spool 23 by pressing it against the inside wall of tube 16 to prevent accidental withdrawal of the floss. There is a hole 31 through the wall of tube 16 through which floss strand 27 can be withdrawn from the tube after passing pad 29.

Rotatably mounted on a pin 34 attached to stick 10 is a withdrawal spool 35 that has a cylindrical receiving portion 37 and a cylindrical knob portion 38. Pin 34 has a rib 34A slightly larger in diameter than opening 36 through stick 10. Pin 34 is of plastic, such as polycarbonate, that is sufficiently resilient to permit rib 34A to reduce in diameter enough so as to be inserted through opening 36 and then substantially recover its initial diameter so as to retain pin 34 on stick 10. As shown in FIG. 2, the right side of rib 34A may be tapered to facilitate entry and passage through opening 36 and the right side may be normal to the pin axis to prevent withdrawal of the pin from opening 36. Pin 34 also has a flange 39 received within a recess 40 in knob 38 to retain spool 35 on the pin. Spool 35 has a flange 41 within a recess 42 in stick 10 and there is a wave washer type spring 43 between stick 10 and flange 41 and bearing thereon to frictionally but yieldably resist rotation of spool 35 relative to stick 10. Tube 16 has a notch 28 for receiving a lug 28A on stick 10 for angularly orienting tube 16 on stick 10 so that opening 31 will be on the same side of stick 10 as spool 35.

Rotatably mounted on a pin 45 attached to stick 11 in the same manner that pin 34 is attached to stick 10 is a collecting spool 46 that has a cylindrical floss receiving portion 47 and a cylindrical knob portion 48. Pin 45 has a flange 49 recieved within a recess 40A in knob 48 to retain spool 46 on the pin. Spool 46 has a flange 52 within recess 52A and there is a wave washer 53 frictionally engaging stick 11 and flange 52 to yieldably resist rotation of spool 46 relative to stick 11.

Knob 48 has a series of axially extending slots 54 on its outer periphery and there is a cylindrical cap 55 having a reduced diameter portion 55A with a bead 55B that may be either a tight press fit in recess 40A of knob 48 to firmly fix the parts together or be a light press fit in such recess so as to be axially movable with moderate force relative to knob 48. Cap 55 has a tapered shoulder 56 adjacent knob 48 to form a wedge shaped groove 56A therebetween. On the periphery of cap 55 is an axially extending and radially projecting surface 57. A metal cutter element 58 is attached to the top surface of cap 55 and has a cutter blade or tap 59 punched partially through the element in predetermined radial alignment with surface 57.

Each of the sticks 10, 11, at their tips 14, 15 have identical openings 62 therethrough for supporting floss strand 27. As shown in FIGS. 6 through 9, the openings 62 may be of varying shape in cross section. Each tip has converging surfaces 63, 64 that form a trough leading to a slit 65 that intersects opening 62. Sticks 10, 11 are preferably made of a plastic such as polycarbonate that has resilient or springy characteristics. The tips 14, 15 are so formed and tempered that the opposite faces of slits 65 are pressed together by spring action of the material of the tips but the material yieldable to permit openings of the slits so that the floss strand can be placed in the troughs and snapped through the slits and into the openings 62. The slits then close to retain the floss in the openings.

The cross section shape of openings 62 is preferably such that floss therein will not be wedged toward the slit by the surfaces adjacent the slit. Thus in FIG. 6 the cross section shape is square with surfaces adjacent the slit being at right angles thereto. In FIG. 7 the cross section shape is such that the surfaces adjacent the slit form an acute angle therewith. In FIG. 8 the cross section shape is circular and the surface portion adjacent the slit would tend to slide the floss toward the slit if the floss is forced upwardly, but immediately adjacent the slit the wedging effect is minimal. In FIG. 9 the slit 65 is slanted and tangent to circular opening 62 so as to intersect the latter at one slide of a vertical centerline of the opening whereby upward motion of the floss strand in the opening will not normally bring the strand to the slit.

To prepare the tool of FIG. 1 for use, the floss strand 27 projecting from opening 31 is wound several times around cylindrical receiving portion 37 of withdrawal spool 35, snapped through slits 65 of tips 14, 15 into openings 62 thereof then wound several times around cylindrical receiving portion 47 of collecting spool 46. From receiving portion 47 it is brought along a slot 54 into wedging groove 56A, to be secured therein and along surface 57 and then into cutter 58 where any excess can be cut off. If cap 55 has a light press fit in knob recess 42 it may move outward slightly when the floss is wound into the wedged shaped groove 56A and may then be pushed in manually to tightly wedge the floss in the wedge shaped groove.

To use the tool after the floss strand has been mounted as described, the person holds a stick by the handle with each hand and with the thumb and forefinger of each hand on the respective withdrawal and collecting spools. The tips 14 and 15 are then inserted in the persons mouth and the floss between the tips passed between two teeth. The sticks are then moved as desired for scrubbing the adjacent side surfaces of the two teeth with the floss.

The operator may now either rotate collecting spool 46 for winding floss onto spool receiving portion 47 and correspondingly shorten the length of floss between tips 14, 15, and hence also shorten the distance between the tips to the desired amount, of the operator may rotate withdrawal spool 35 for pulling floss from tube 16 to make more floss available between tips 14, 15 and thus lengthen the space therebetween. Turning both spools at once and at the same rate causes fresh floss to advance into the space between tips 14, 15 without effecting the length of such space. Turning of either spool or of both spools simultaneously is easily accomplished with the thumb and forefinger of the respective hand while the remaining fingers grasp the respective handles 12, 13. Thus shortening, lengthening or advancing the floss in the work space between tips 14, 15 can be readily accomplished even while the tips are within the person's mouth.

It has been found that floss strand as heretofore obtainable has about three 360° twists per inch, as shown in FIG. 11 so that the individual filaments 69 describe a spiral. This causes the strand to be substantially cylindrical in cross section with the strand having a width much larger than the individual filaments. Such floss may be difficult to insert between a person's teeth when the teeth fit closely against each other. It has been found that if the twist is removed so that the individual filaments lie parallel to the longitudinal axis of the strand, as shown in FIG. 10, the strand will be flat or ribbon shaped, as shown, with a thickness that may be on the order of 0.0005". Such a flat strand, when presented edgewise, will be easier to insert between closely fitting teeth. Thus, as part of this invention, it is contemplated that supply spool 23 has untwisted floss thereon and that the spool with the coil of floss thereon is permitted to rotate when withdrawing the floss so that the strand, as floss is being withdrawn, does not pass over the axis of the spool whereby the strand remains untwisted. If the strand is withdrawn in a manner to permit it to pass over the spool axis, a 360° twist is imparted each time the supply spool makes one revolution.

It is also comtemplated that the floss can be loaded in hollow coil form within tube 16 and with spool 23 omitted, as shown in FIG. 12. In such case the floss is first wound without twisting of the strand upon a length of rod for a distance corresponding generally to the length of spool 23 between flanges 24, 25 to a coil diameter less than the inside diameter of tube 16 and then removed in this form from the rod and inserted into the tube. In such case, one end of the strand lies along the inside of the coil and the other along the outside. The end along the inside is fed past pad 29A to be frictionally engaged thereby and through opening 31 of tube 16 to the exterior.

Tube caps 17 and 17A, and/or collecting spool caps 55, 73, and/or spools 35, 46 may be made in several different colors of plastic material so that each member of a family may have a different color and thus be able to readily identify his or her tool. Coloring of spool 46 and cap 55 also provides a contrast with white floss so that threading of the floss along notches 54 and 57 may be more easily seen.

In the modified form of the collecting spool 70 shown in FIGS. 14, 15, and 16, pin 45 is like that of FIG. 4 and spool knob 71 is formed with circumferentially spaced axially extending grooves 80 in its outer surface and a ring 81 is press fitted into cylindrical recess 82 of knob 71 so that in effect it becomes an integral part thereof. Formed integrally with ring 81 by means of a thin hinge section 72 is a cap 73. The ring and cap are formed of a relatively soft plastic material such as polyethylene that yields and bends readily so that hinge 72 will easily bend to permit the cap to be swung to open and closed positions relative to ring 81 by means of a tab 74. In the open position a cylindrical portion 75 of cap 73 is withdrawn from cylindrical bore 76 of ring 81 and floss strand 27, after being unwound from receiving portion 77 and led through one of the grooves 80, is laid diametrically across the open end of ring 81. Cap 73 is then swung to closed position in which cylindrical portion 75 enters bore 76 with a snug fit. In the closed position of cap 73, the floss strand 27 is tightly wedged between the wall of bore 76 and cap cylindrical portion 75 on diametrically opposite sides of the bore, as shown in FIG. 16. The strand may then be led through the cutter 79, as shown in FIG. 14, and cut off.

In another form of the invention illustrated in FIG. 17 the tool body means includes a member 92 and two sticks 93 and 94 that are integrally or rigidly attached to member 92. A tube 16, corresponding to tubes 16 of FIGS. 2 and 12 is mounted on member 92 in the same manner as in either of the latter two figures. Withdrawal spool 35 corresponding to spool 35 of FIG. 3 and collecting spool 95 corresponding to either of spools 46 or 70, and operating in the same manner, are mounted in the body means.

In another form of the invention, not shown, one of the sticks 93, 94 of FIG. 17 may be pivotally attached to member 92 for varying the distance between tips 14, 15 and with a set screw or other device for locking the adjustable stick in a set position relative to the other stick. Spool 35 or 95, as the case may be, may then be mounted on the corresponding pivoted stick 93 or 94, or it may be mounted on member 92.

In the modified form of the collecting spool shown in FIGS. 18 and 19, plastic spool member 101 is a single piece except for the metal cutter 122. Spool 101 has a cylindrical shank 103 rotatably fitted within bore 104 in body 10 and having a flange 106 within body counterbore 107. At its lower end shank 103 has a bore 108, a rib 109, a conical surface 110 and several transverse slits 111 that form a plurality of fingers 112. When inserting shank 103 into bore 104, conical surface 110 engages the upper end of the wall of bore 104 to cam fingers 112 radially inward so that rib 109 may enter bore 104. Upon rib 109 reaching counterbore 113 the fingers spring outward to engage rib 109 with transverse wall 114 of the body for retaining spool 101 on body 10.

At its upper end spool 101 has a knob 115 with several axially extending slots 116 in its outer periphery and there is a cylindrical section 117 between knob 115 and flange 106.

Knob 115 has a cylindrical recess 120 into which is press fitted a cutter 121 that has an upward bent tab 122 similar to tab 59 in FIG. 4. Within recess 120 knob 115 has an upwardly extending projection 125 whose upper surface 126 engages tab 122.

When spool 101 is in use, the floss strand 27 is wrapped about cylindrical portion 117 for several turns then brought upwardly through a slot 116 and under tab 122 to be wedged between the tab and projection 125. The strand may then be cut by the tab at point 127 beyond the wedged portion. After being thus cut, the strand remains to be wedged between the tab and projection 125 so that the strand will not become unravelled from the spool.

In another form of the invention, slits 111 may be omitted from the lower end of spool 101 in FIG. 18 but with bore 108 retained. In this case the lower end of spool 101 has a continuous circumference and because of the resilience of the plastic, such as polycarbonate, from which it is made, such lower end will contract radially an amount sufficient for rib 109 to pass through bore 104 when assembling the spool 101 to body 10 and the rib 109 will then spring radially outwardly into counterbore 113 to engage shoulder 114.

I claim:

1. A flossing tool comprising a body means, tip means on the body means for supporting floss in a position for use in a person's mouth, storage means on the body means on one side of said tip means for storing a supply of said floss; a floss collecting spool separate and independent of the storage means mounted on the body means on the other side of the tip means for yieldable rotation in either angular direction independently of the storage means and having an exposed circumferential receiving portion upon which floss leading from said tip means may be wound by rotation of said collecting spool in one angular direction and unwound therefrom upon rotation of the spool in the other angular direction.

2. The tool of claim 1 in which said collecting spool has a knob grippable by a person's fingers for freely rotating the spool relatively to the storage means, and said collecting spool carrying a securing means spaced from said receiving portion for securing the floss to the spool, and axially extending guide means on the spool between the receiving portion and the securing means for guiding the floss therebetween.

3. A flossing tool having a body means, tip means on the body means for supporting a portion of the floss in a position for use in a person's mouth, an enclosed storage a supply of floss, a withdrawal spool independent of the storage means and mounted on the body means for independent rotation in either angular direction, means on the spool for manual rotation of the same, said spool having an exposed receiving portion upon which a part of the floss may be wound, said withdrawal spool being mounted on the body means between the tip means and the storage means whereby floss from the supply may be wound upon the receiving portion and then directed to one side of the tip means and whereby subsequent rotation of the spool in one direction withdraws floss from the storage means and feeds it to the tip means and rotation in the other direction retracts floss from the tip means.

4. A flossing tool in accordance with claim 3 in which there is a collecting spool separate and independent of the withdrawl spool mounted on the body means and having a receiving portion to receive floss from the other side of said tip means said collecting spool being mounted on the body means for yieldably rotation in either direction independently of the withdrawal spool, and means on the collecting spool for manually rotating the same.

5. The tool of claim 17 in which there is a tube removably mounted on the body means and providing a chamber to receive a supply of floss, the withdrawal spool having its rotational axis normal to the axis of said tube an opening in the wall of the tube through which the floss may be led from the tube to said receiving portion of said withdrawal spool, and interengaging means on the tube and body means for angularly orienting the tube on the body whereby said opening has a predetermined angular orientation with respect to said rotational axis of said spool.

6. A flossing tool including a body means that provides a pair of sticks, each stick having a tip with means thereon for supporting a strand of floss, said means on one of said tips including an opening through which a strand of floss may be passed, and slit in said one tip leading from an exterior surface thereof to said opening and through which slit the floss may be passed for insertion into said opening, the faces of said tip on opposite sides of said slit being normally in contact with each other, and the material of said one tip is springy whereby said faces may be separated to pass the floss through the slit and are then brought together by the spring action of said material.

7. The tool of claim 6 in which said slit enters said opening at one side of a plane extending longitudinally of the stick having said one tip and containing the central axis of said opening.

8. The tool of claim 1 in which a cutter is mounted on the collecting spool, said cutter having an edge to which the strand of floss may be led from said receiving portion for severing of the strand, wedging means on the spool between said portion and said edge whereby the strand may be wedged in the wedging means to be gripped thereby prior to severing of the strand by the cutting edge and whereby the strand remains gripped by the wedging means after such severing.

9. The tool of claim 4 in which said body has a bore and having a first transverse surface surrounding the bore at one end thereof and a second transverse surface surrounding the bore at the other end thereof, one of said spools having a shaft rotatably mounted in said bore and having first and second radially projecting portions at each end of the shaft and projecting radially beyond said bore to be engaged with said transverse surfaces for retaining the spool within said body, said shaft having a hollow portion at one end thereof and said first radially projecting portion being radially opposite said hollow portion and being contractible to a diameter no greater than that of said bore to permit insertion through said bore and being springable to a diameter larger than said bore after such insertion to project radially beyond said bore as aforesaid.

* * * * *

UNITED STATES PATENT AND TRADEMARK OFFICE
CERTIFICATE OF CORRECTION

PATENT NO. : 4,151,851
DATED : MAY 1, 1979
INVENTOR(S) : KENNETH R. BRAGG

It is certified that error appears in the above-identified patent and that said Letters Patent are hereby corrected as shown below:

In column 6, line 55, after "age", insert---means on the body means for storing---

In column 7, line 10, change "17" to---3---.

Signed and Sealed this

Sixth Day of November 1979

[SEAL]

Attest:

RUTH C. MASON
*Attesting Officer*

LUTRELLE F. PARKER
*Acting Commissioner of Patents and Trademarks*